US012060370B2

(12) United States Patent
Leoncini et al.

(10) Patent No.: US 12,060,370 B2
(45) Date of Patent: *Aug. 13, 2024

(54) MOLYBDENUM (0) PRECURSORS FOR DEPOSITION OF MOLYBDENUM FILMS

(71) Applicants: Applied Materials, Inc., Santa Clara, CA (US); National University of Singapore, Singapore (SG)

(72) Inventors: Andrea Leoncini, Singapore (SG); Paul Mehlmann, Singapore (SG); Nemanja Dordevic, Singapore (SG); Han Vinh Huynh, Singapore (SG); Doreen Wei Ying Yong, Singapore (SG); Mark Saly, Santa Clara, CA (US); Bhaskar Jyoti Bhuyan, San Jose, CA (US)

(73) Assignee: Applied Materials, Inc., Santa Clara, CA (US)

( * ) Notice: Subject to any disclaimer, the term of this patent is extended or adjusted under 35 U.S.C. 154(b) by 289 days.

This patent is subject to a terminal disclaimer.

(21) Appl. No.: 17/146,878

(22) Filed: Jan. 12, 2021

(65) Prior Publication Data
US 2022/0220139 A1   Jul. 14, 2022

(51) Int. Cl.
C07F 11/00   (2006.01)
C23C 16/02   (2006.01)
C23C 16/455  (2006.01)
C23C 16/56   (2006.01)

(52) U.S. Cl.
CPC .......... *C07F 11/00* (2013.01); *C23C 16/0209* (2013.01); *C23C 16/0227* (2013.01); *C23C 16/0254* (2013.01); *C23C 16/45527* (2013.01); *C23C 16/56* (2013.01)

(58) Field of Classification Search
CPC .. C07D 213/22; C07D 255/02; C07D 453/02; C23C 16/18; C07F 11/00; C07F 9/5045
See application file for complete search history.

(56) References Cited

U.S. PATENT DOCUMENTS 7,001,831 B2 * 2/2006 Niira ............... C23C 16/345
                                      257/E21.101
11,584,768 B2 * 2/2023 Leoncini ............ C23C 16/405

FOREIGN PATENT DOCUMENTS

WO   2020076502 A1   4/2020
WO   2020185618 A1   9/2020

OTHER PUBLICATIONS

DuBois (Inorganic Chemistry; vol. 9, No. 4, 1970, 968-970).*
Backes-Dahmann, Gabriele , et al., "Preparation and Electrochemical investigation of Monomeric Complexes of Molybdenum(O-VI) with the Ligand I,4,7-Trimethyl-1,4,7-triazacyclononane (L). Crystal Structure of [MoIVLBr3](PF6)", Inorganic Chemistry, vol. 24, No. 4, 1985.
Cloke, F. , et al., "Synthesis of Zerov Alent Tris[Bis(1,2-(Dimethylphospidno)Ethane] Compounds of Chromium, Molybdenum, Tungsten, Vanadium, Niobium and Tantalum Using the Metal Vapours", Journal of Organometallic Chemistry, 198 (1980) C69-C71.
Malkov, Andrei V., et al., "Synthesis of New Chiral 2,2¢-Bipyridyl-Type Ligands, Their Coordination to Molybdenum (0), Copper(II), and Palladium(II), and Application in Asymmetric Allylic Substitution, Allylic Oxidation, and Cyclopropanation", Organometallics 2001, 20, 673-690.
PCT International Search Report and Written Opinion in PCT/US2022/011797 dated Apr. 29, 2022, 11 pages.
Bezdek, M. J., et al., "Coordination-induced weakening of ammonia, water, and hydrazine X-H bonds in a molybdenum complex", Science, 2016, vol. 354, No. 6313, pp. 730-733.
Diskus, M. , et al., "Growth of thin films of molybdenum oxide by atomic layer deposition", Journal of materials chemistry, 2011, vol. 21, No. 3, pp. 705-710.
Sattler, A. , "Chemistry of highly reactive group 5 and 6 transition metal compounds: modeling aspects of the Industrial hydrotreating process and synthesis of the first transition metal complexes that feature a [CCC] X3-donor pincer ligand", in partial fulfillment of the requirements for the degree of doctor of philosophy in the graduate school of arts and sciences, Columbia university, 2012, pp. 1-452.
Wang, Y. , et al., "Interaction of molybdenum hexacarbonyl with metallic aluminum at high temperatures: carbide and alloy formation", Journal of molecular catalysis A: Chemical, 2005, vol. 236, pp. 18-31.
Zhu, G. , et al., "Oxidative addition of dihydrogen to (16-Arene)Mo(PMe3)3 complexes: origin of the naphthalene and anthracene effects", Journal of the american chemical society, 2006, vol. 128, No. 16, pp. 5452-5461.
Green, Malcolm L.H., et al., "A Comparison of the Rates of Intramolecular Hydrogen Migration in the Molecules [Mo(n-C7 H8) 2 ]n+ to give [Mo (n-C7 H7 )(n-C7 H9 )n+,n = 0 or 1: Crystal Structures of [MO(n-C7 H8 ) 2 ], [Mo(n-C7 H7 ) (n-C7 H9 )], and [Mo(n-C7 H8) 2 ] [BF4 ]", J. Chem. Soc. Dalton Trans. 1989, pp. 331-343.

(Continued)

*Primary Examiner* — Pancham Bakshi
(74) *Attorney, Agent, or Firm* — Servilla Whitney LLC

(57) ABSTRACT

Molybdenum(0) coordination complexes comprising ligands which each coordinate to the metal center by nitrogen or phosphorous are described. Methods for depositing molybdenum-containing films on a substrate are described. The substrate is exposed to a molybdenum precursor and a reactant to form the molybdenum-containing film (e.g., elemental molybdenum, molybdenum oxide, molybdenum carbide, molybdenum silicide, molybdenum nitride). The exposures can be sequential or simultaneous.

1 Claim, 3 Drawing Sheets

(56) References Cited

OTHER PUBLICATIONS

Green, Jennifer C., et al., "Molybdenum-95 and Carbon-13 Nuclear Magnetic Shielding and Bonding Relationships in Sandwich Complexes", J. Chem. Soc. Dalton Trans. 1986, pp. 1313-1316.

Green, Malcolm L.H., et al., "New Synthetic Pathways in n-Cycloheptatrienyl Molybdenum Chemistry", J. Chem. Soc., Chem. Commun., 1992, pp. 918-919.

Green, Malcolm L.H., et al., "Synthesis and Reactions of n-Cycloheptatrienyl Derivatives of Molybdenum", J. Chem. Soc. Dalton Trans. 1993, pp. 3203-3212.

* cited by examiner

MOLYBDENUM (0) PRECURSORS FOR DEPOSITION OF MOLYBDENUM FILMS

TECHNICAL FIELD

Embodiments of the disclosure relate to molybdenum precursors and methods for depositing molybdenum-containing films. More particularly, embodiments of the disclosure are directed to molybdenum(0) precursors containing nitrogen and phosphorous based ligands and methods of use thereof.

BACKGROUND

The semiconductor processing industry continues to strive for larger production yields while increasing the uniformity of layers deposited on substrates having larger surface areas. These same factors in combination with new materials also provide higher integration of circuits per unit area of the substrate. As circuit integration increases, the need for greater uniformity and process control regarding layer thickness rises. As a result, various technologies have been developed to deposit layers on substrates in a cost-effective manner, while maintaining control over the characteristics of the layer.

Chemical vapor deposition (CVD) is one of the most common deposition processes employed for depositing layers on a substrate. CVD is a flux-dependent deposition technique that requires precise control of the substrate temperature and the precursors introduced into the processing chamber in order to produce a desired layer of uniform thickness. These requirements become more critical as substrate size increases, creating a need for more complexity in chamber design and gas flow technique to maintain adequate uniformity.

A variant of CVD that demonstrates excellent step coverage is cyclical deposition or atomic layer deposition (ALD). Cyclical deposition is based upon atomic layer epitaxy (ALE) and employs chemisorption techniques to deliver precursor molecules on a substrate surface in sequential cycles. The cycle exposes the substrate surface to a first precursor, a purge gas, a second precursor and the purge gas. The first and second precursors react to form a product compound as a film on the substrate surface. The cycle is repeated to form the layer to a desired thickness.

The advancing complexity of advanced microelectronic devices is placing stringent demands on currently used deposition techniques. Unfortunately, there is a limited number of viable chemical precursors available that have the requisite properties of robust thermal stability, high reactivity, and vapor pressure suitable for film growth to occur. In addition, precursors that often meet these requirements still suffer from poor long-term stability and lead to thin films that contain elevated concentrations of contaminants such as oxygen, nitrogen, and/or halides that are often deleterious to the target film application.

Molybdenum and molybdenum based films have attractive material and conductive properties. These films have been proposed and tested for applications from front end to back end parts of semiconductor and microelectronic devices. Processing a molybdenum precursor often involves use of halogen and carbonyl-based substituents. These ligands provide sufficient stability at the expense of reduced reactivity, increasing process temperature. Other molybdenum precursors include amide ligands, which can cause nitride impurities. There is, therefore, a need in the art for molybdenum precursors that are free of halogen and carbonyl groups that react to form molybdenum metal and molybdenum based films.

SUMMARY

One or more embodiments of the disclosure are directed to metal coordination complexes comprising molybdenum (0) and one or more ligands, each ligand coordinated by nitrogen or phosphorous.

Additional embodiments of the disclosure are directed to a method of depositing a film. The method comprises exposing a substrate to a molybdenum(0) precursor comprising one or more ligands. Each ligand is coordinated by nitrogen or phosphorous. The substrate is exposed to a reactant to react with molybdenum(0) precursor to form a molybdenum film on the substrate.

Further embodiments of the disclosure are directed to a method of depositing a film. The method comprises forming a molybdenum-containing film in a process cycle comprising sequential exposure of a substrate to a molybdenum(0) precursor, purge gas, reactant, and purge gas. The molybdenum(0) precursor comprises one or more ligands, each ligand coordinated by nitrogen or phosphorous.

BRIEF DESCRIPTION OF THE DRAWINGS

So that the manner in which the above recited features of the disclosure can be understood in detail, a more particular description of the disclosure, briefly summarized above, may be had by reference to embodiments, some of which are illustrated in the appended drawings. It is to be noted, however, that the appended drawings illustrate only typical embodiments of the disclosure and are therefore not to be considered limiting of its scope, for the disclosure may admit to other equally effective embodiments.

DETAILED DESCRIPTION

Figure 1:
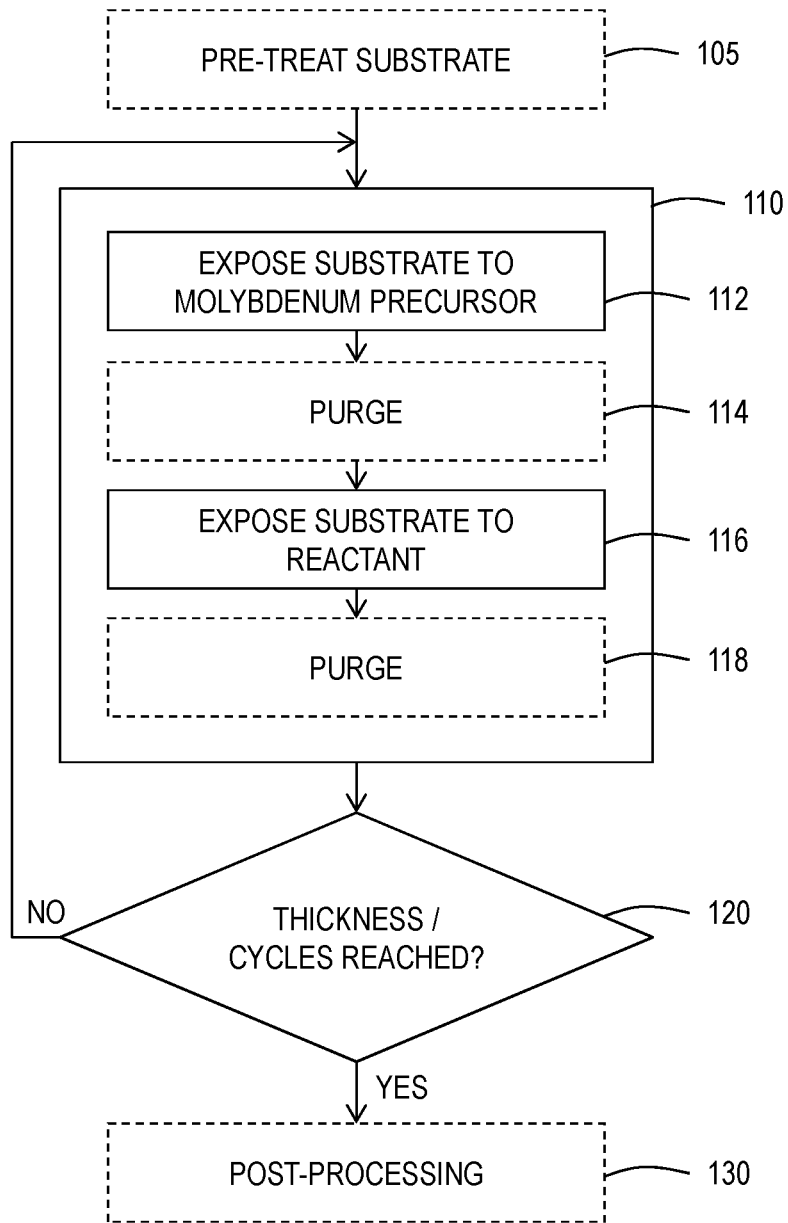
FIG. 1 illustrates a process flow diagram of a method in accordance with one or more embodiments of the disclosure.

Before describing several exemplary embodiments of the invention, it is to be understood that the invention is not limited to the details of construction or process steps set forth in the following description. The invention is capable of other embodiments and of being practiced or being carried out in various ways.

Embodiments of the disclosure provide precursors and processes for depositing molybdenum-containing films. The precursor comprises a metal coordination complex. The metal coordination complexes of one or more embodiments are substantially free of halogens and carbonyl groups. Monodentate, bidentate and tridentate neutral ligands comprising nitrogen and phosphorous are used under ALD and CVD conditions. The process of various embodiments uses vapor deposition techniques, such as an atomic layer deposition (ALD) or chemical vapor deposition (CVD) to provide molybdenum films. The molybdenum precursors of one or more embodiments are volatile and thermally stable, and, thus, suitable for vapor deposition.

The molybdenum coordination complexes of one or more embodiments are substantially free of halogen and carbonyl groups. As used herein, the term "substantially free" means that there is less than about 5%, including less than about 4%, less than about 3%, less than about 2%, less than about 1%, and less than about 0.5% of halogen, on an atomic basis, in the molybdenum coordination complexes. In some embodiments, the molybdenum coordination complexes are substantially free of carbonyl groups, and there is less than about 5%, including less than about 4%, less than about 3%, less than about 2%, less than about 1%, and less than about 0.5% of carbonyl group, on an atomic basis, in the molybdenum coordination complexes.

A "substrate" as used herein, refers to any substrate or material surface formed on a substrate upon which film processing is performed during a fabrication process. For example, a substrate surface on which processing can be performed include materials such as silicon, silicon oxide, strained silicon, silicon on insulator (SOI), carbon doped silicon oxides, amorphous silicon, doped silicon, germanium, gallium arsenide, glass, sapphire, and any other materials such as metals, metal nitrides, metal alloys, and other conductive materials, depending on the application. Substrates include, without limitation, semiconductor wafers. Substrates may be exposed to a pretreatment process to polish, etch, reduce, oxidize, hydroxylate, anneal and/or bake the substrate surface. In addition to film processing directly on the surface of the substrate itself, in the present invention, any of the film processing steps disclosed may also be performed on an underlayer formed on the substrate as disclosed in more detail below, and the term "substrate surface" is intended to include such underlayer as the context indicates. Thus, for example, where a film/layer or partial film/layer has been deposited onto a substrate surface, the exposed surface of the newly deposited film/layer becomes the substrate surface.

According to one or more embodiments, the method uses an atomic layer deposition (ALD) process. In such embodiments, the substrate surface is exposed to the precursors (or reactive gases) sequentially or substantially sequentially. As used herein throughout the specification, "substantially sequentially" means that a majority of the duration of a precursor exposure does not overlap with the exposure to a co-reagent, although there may be some overlap.

As used in this specification and the appended claims, the terms "precursor", "reactant", "reactive gas" and the like are used interchangeably to refer to any gaseous species that can react with the substrate surface.

"Atomic layer deposition" or "cyclical deposition" as used herein refers to the sequential exposure of two or more reactive compounds to deposit a layer of material on a substrate surface. As used in this specification and the appended claims, the terms "reactive compound", "reactive gas", "reactive species", "precursor", "process gas" and the like are used interchangeably to mean a substance with a species capable of reacting with the substrate surface or material on the substrate surface in a surface reaction (e.g., chemisorption, oxidation, reduction). The substrate, or portion of the substrate is exposed sequentially to the two or more reactive compounds which are introduced into a reaction zone of a processing chamber. In a time-domain ALD process, exposure to each reactive compound is separated by a time delay to allow each compound to adhere and/or react on the substrate surface. In a spatial ALD process, different portions of the substrate surface, or material on the substrate surface, are exposed simultaneously to the two or more reactive compounds so that any given point on the substrate is substantially not exposed to more than one reactive compound simultaneously. As used in this specification and the appended claims, the term "substantially" used in this respect means, as will be understood by those skilled in the art, that there is the possibility that a small portion of the substrate may be exposed to multiple reactive gases simultaneously due to diffusion, and that the simultaneous exposure is unintended.

In one aspect of a time-domain ALD process, a first reactive gas (i.e., a first precursor or compound A) is pulsed into the reaction zone followed by a first time delay. Next, a second precursor or compound B is pulsed into the reaction zone followed by a second delay. During each time delay a purge gas, such as argon, is introduced into the processing chamber to purge the reaction zone or otherwise remove any residual reactive compound or by-products from the reaction zone. Alternatively, the purge gas may flow continuously throughout the deposition process so that only the purge gas flows during the time delay between pulses of reactive compounds. The reactive compounds are alternatively pulsed until a desired film or film thickness is formed on the substrate surface. In either scenario, the ALD process of pulsing compound A, purge gas, compound B and purge gas is a cycle. A cycle can start with either compound A or compound B and continue the respective order of the cycle until achieving a film with the desired thickness.

In an aspect of a spatial ALD process, a first reactive gas and second reactive gas (e.g., hydrogen radicals) are delivered simultaneously to the reaction zone but are separated by an inert gas curtain and/or a vacuum curtain. The substrate is moved relative to the gas delivery apparatus so that any given point on the substrate is exposed to the first reactive gas and the second reactive gas.

Without intending to be bound by theory, it is thought that the presence of halogens, carbonyls groups, and, in some case, oxygen, in the structure of molybdenum (Mo) precursors can pose challenges, as halogen and oxygen contamination may affect device performance and hence require additional removal procedures. Carbonyl (CO) binds strongly to metals, requiring higher thermal budget, or the use of additional reagents for its removal. Carbonyl (CO) can redeposit and poison other metal surfaces.

Molybdenum (Mo) can be grown by atomic layer deposition or chemical vapor deposition for many applications. One or more embodiments of the disclosure advantageously provide processes for atomic layer deposition or chemical vapor deposition to form molybdenum-containing films. As used in this specification and the appended claims, the term "molybdenum-containing film" refers to a film that comprises molybdenum atoms and has greater than or equal to about 1 atomic % molybdenum, greater than or equal to about 2 atomic % molybdenum, greater than or equal to about 3 atomic % molybdenum, greater than or equal to about 4 atomic % molybdenum, greater than or equal to about 5 atomic % molybdenum, greater than or equal to about 10 atomic % molybdenum, greater than or equal to about 15 atomic % molybdenum, greater than or equal to about 20 atomic % molybdenum, greater than or equal to about 25 atomic % molybdenum, greater than or equal to about 30 atomic % molybdenum, greater than or equal to about 35 atomic % molybdenum, greater than or equal to about 40 atomic % molybdenum, greater than or equal to about 45 atomic % molybdenum, greater than or equal to about 50 atomic % molybdenum, or greater than or equal to about 60 atomic % molybdenum. In some embodiments, the molybdenum-containing film comprises one or more of molybdenum metal (elemental molybdenum), molybdenum oxide ($MoO_2$, $MoO_3$), molybdenum carbide (MoC, $Mo_2C$), molybdenum silicide ($MoSi_2$), or molybdenum nitride (Mo₂N). The skilled artisan will recognize that the use of molecular formula like MoSi$_x$ does not imply a specific stoichiometric relationship between the elements but merely the identity of the major components of the film. For example, MoSi$_x$ refers to a film whose major composition comprises molybdenum and silicon atoms. In some embodiments, the major composition of the specified film (i.e., the sum of the atomic percents of the specified atoms) is greater than or equal to about 95%, 98%, 99% or 99.5% of the film, on an atomic basis.

With reference to FIG. 1, one or more embodiments of the disclosure are directed to method 100 of depositing a film. The method illustrated in FIG. 1 is representative of an atomic layer deposition (ALD) process in which the substrate or substrate surface is exposed sequentially to the reactive gases in a manner that prevents or minimizes gas phase reactions of the reactive gases. In some embodiments, the method comprises a chemical vapor deposition (CVD) process in which the reactive gases are mixed in the processing chamber to allow gas phase reactions of the reactive gases and deposition of the thin film.

In some embodiments, the method 100 includes a pre-treatment operation 105. The pre-treatment can be any suitable pre-treatment known to the skilled artisan. Suitable pre-treatments include, but are not limited to, pre-heating, cleaning, soaking, native oxide removal, or deposition of an adhesion layer (e.g. titanium nitride (TiN)). In one or more embodiments, an adhesion layer, such as titanium nitride, is deposited at operation 105. In other embodiments, molybdenum can be integrated without the need for an adhesion liner.

At deposition 110, a process is performed to deposit a molybdenum-containing film on the substrate (or substrate surface). The deposition process can include one or more operations to form a film on the substrate. In operation 112, the substrate (or substrate surface) is exposed to a molybdenum precursor to deposit a film on the substrate (or substrate surface). The molybdenum precursor can be any suitable molybdenum-containing compound that can react with (i.e., adsorb or chemisorb onto) the substrate surface to leave a molybdenum-containing species on the substrate surface.

Current molybdenum precursors for ALD of metallic films use halogen and carbonyl-based ligands, which provide sufficient stability at the expense of reduced reactivity, increasing process temperature. Amide ligands can cause nitride impurities. Accordingly, one or more embodiments use neutral nitrogen and phosphorous coordinating ligands. These ligands provide molybdenum precursors with improved thermal stability, while retaining high volatility and producing molybdenum-containing films with minimum impurities.

Unless otherwise indicated, the term "lower alkyl," "alkyl," or "alk" as used herein alone or as part of another group includes both straight and branched chain hydrocarbons, containing 1 to 20 carbons, 1 to 10 carbons, 1 to 6 carbons or 1 to 4 carbons in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof, and the like. Such groups may optionally include up to 1 to 4 substituents. The alkyl may be substituted or unsubstituted.

In one or more embodiments, the molybdenum precursor has a general formula of Mo(1)$_x$(L2)$_y$(L3)$_z$ where L1 is one or more neutral monodentate ligand, L2 is one or more neutral bidentate ligand, L3 is one or more neutral tridentate ligand, x is 0 to 8, y is 0 to 4, z is 0 to 2 and x+2y+3z is in a range of 4 to 8. In some embodiments, x+2y+3z is equal to 6. The ligands each coordinate by nitrogen or phosphorous. Each class of ligand (e.g., monodentate) may be homogenous or comprise different ligands of the same class.

Figure 2A:
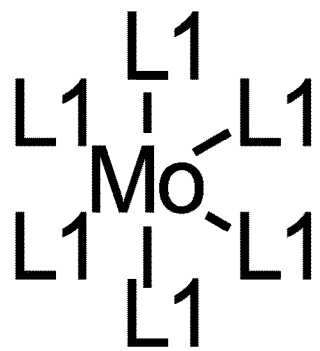
FIGS. 2A-2C illustrate exemplary metal complexes in accordance with one or more embodiments of the disclosure.
Figure 2B:
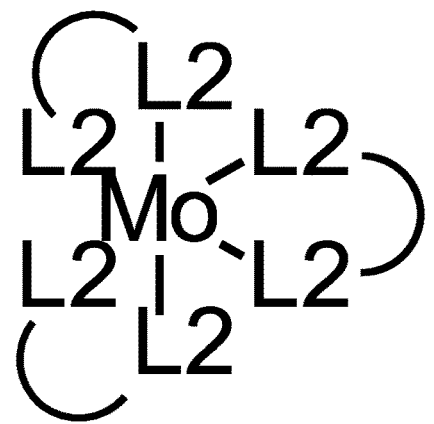
Figure 2C:
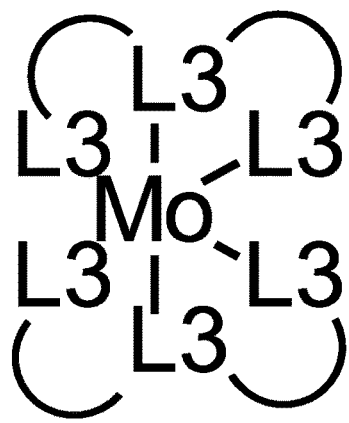

In one or more embodiments, the molybdenum precursor, as shown in FIG. 2A, comprises six monodentate ligands. In one or more embodiments, the molybdenum precursor, as shown in FIG. 2B, comprises 3 bidentate ligands. In one or more embodiment, the molybdenum precursor, as shown in FIG. 2C, comprises 2 tridentate ligands. In some embodiments, the molybdenum precursor comprises a combination of monodentate, bidentate and/or tridentate ligands.

In some embodiments, the monodentate ligand is selected from one or more of:

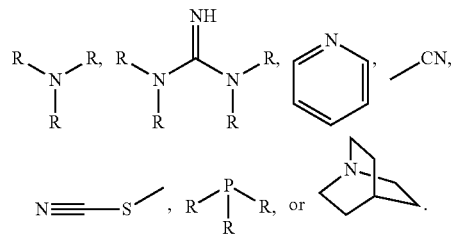

In some embodiments, the bidentate ligand is selected from one or more of:

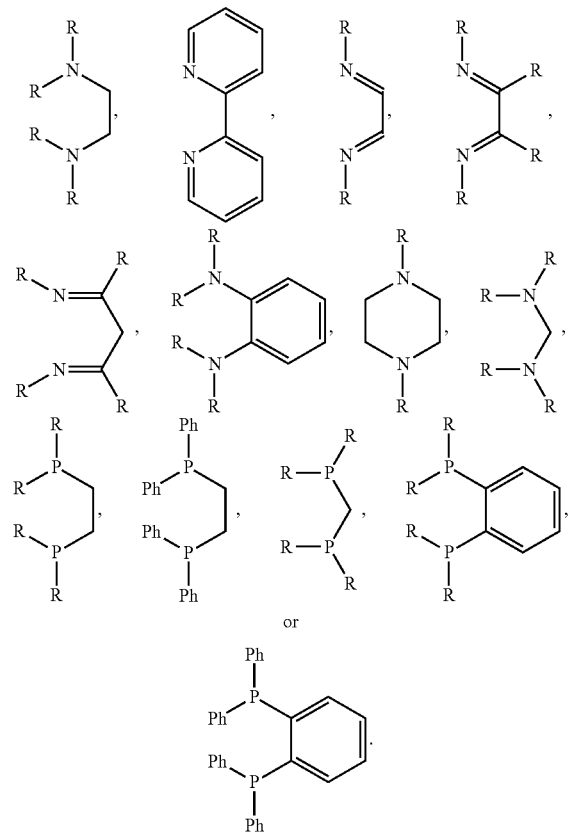

In some embodiments, the tridentate ligand is selected from one or more of:

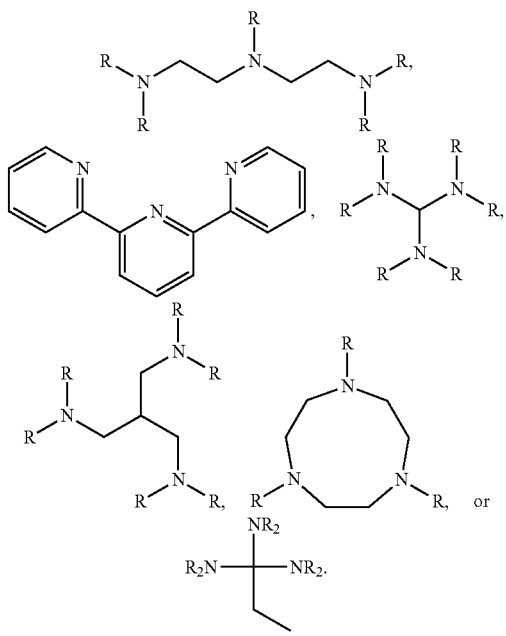

In one or more embodiments, each R may be independently selected from Me-, Et-, iPr-, and tBu-substituents.

Without intending to be bound by theory, it is thought that each of the ligands disclosed herein coordinates to the molybdenum metal center through the nitrogen or phosphorous atoms of the ligand. Each ligand is expected to impact the volatility and thermal stability of the metal complex. Accordingly, it is expected that through the judicious selection of ligands, a metal precursor with preferred thermal properties may be produced and used to deposit a molybdenum-containing layer by CVD or ALD.

As used herein, a "substrate surface" refers to any substrate surface upon which a layer may be formed. The substrate surface may have one or more features formed therein, one or more layers formed thereon, and combinations thereof. The substrate (or substrate surface) may be pretreated prior to the deposition of the molybdenum-containing layer, for example, by polishing, etching, reduction, oxidation, halogenation, hydroxylation, annealing, baking, or the like.

The substrate may be any substrate capable of having material deposited thereon, such as a silicon substrate, a III-V compound substrate, a silicon germanium (SiGe) substrate, an epi-substrate, a silicon-on-insulator (SOI) substrate, a display substrate such as a liquid crystal display (LCD), a plasma display, an electro luminescence (EL) lamp display, a solar array, solar panel, a light emitting diode (LED) substrate, a semiconductor wafer, or the like. In some embodiments, one or more additional layers may be disposed on the substrate such that the molybdenum-containing layer may be at least partially formed thereon. For example, in some embodiments, a layer comprising a metal, a nitride, an oxide, or the like, or combinations thereof may be disposed on the substrate and may have the molybdenum containing layer formed upon such layer or layers.

At operation 114, the processing chamber is optionally purged to remove unreacted molybdenum precursor, reaction products and by-products. As used in this manner, the term "processing chamber" also includes portions of a processing chamber adjacent the substrate surface without encompassing the complete interior volume of the processing chamber. For example, in a sector of a spatially separated processing chamber, the portion of the processing chamber adjacent the substrate surface is purged of the molybdenum precursor by any suitable technique including, but not limited to, moving the substrate through a gas curtain to a portion or sector of the processing chamber that contains none or substantially none of the molybdenum precursor. In one or more embodiments, purging the processing chamber comprises applying a vacuum. In some embodiments, purging the processing chamber comprises flowing a purge gas over the substrate. In some embodiments, the portion of the processing chamber refers to a micro-volume or small volume process station within a processing chamber. The term "adjacent" referring to the substrate surface means the physical space next to the surface of the substrate which can provide sufficient space for a surface reaction (e.g., precursor adsorption) to occur. In one or more embodiments, the purge gas is selected from one or more of nitrogen ($N_2$), helium (He), and argon (Ar).

At operation 116, the substrate (or substrate surface) is exposed to a reactant to form one or more of a molybdenum film on the substrate. The reactant can react with the molybdenum-containing species on the substrate surface to form the molybdenum-containing film. In some embodiments, the reactant comprises a reducing agent. In one or more embodiments, the reducing agent can comprise any reducing agent known of to one of skill in the art. In other embodiments, the reactant comprises an oxidizing agent.

In one or more embodiments, the oxidizing agent can comprise any oxidizing agent known to one of skill in the art. In further embodiments, the reactant comprises one or more oxidizing agent and a reducing agent.

In specific embodiments, the reactant is selected from one or more of 1,1-dimethylhydrazine (DMH), alkyl amine, hydrazine, alkyl hydrazine, allyl hydrazine, hydrogen ($H_2$), ammonia ($NH_3$), alcohols, water ($H_2O$), oxygen ($O_2$), ozone ($O_3$), nitrous oxide ($N_2O$), nitrogen dioxide ($NO_2$), peroxides, and plasmas thereof. In some embodiments, the alkyl amine is selected from one or more of tert-butyl amine ($tBuNH_2$), isopropyl amine ($iPrNH_2$), ethylamine ($CH_3CH_2NH_2$), diethylamine (($CH_3CH_2)_2NH$), or butyl amine ($BuNH_2$). In some embodiments, the reactant comprises one or more of compounds with the formula $R'NH_2$, $R'_2NH$, $R'_3N$, $R'_2SiNH_2$, $(R'_3Si)_2NH$, $(R'_3Si)_3N$; where each R' is independently H or an alkyl group having 1-12 carbon atoms. In some embodiments, the alkyl amine consists essentially of one or more of tert-butyl amine ($tBuNH_2$), isopropyl amine ($iPrNH_2$), ethylamine ($CH_3CH_2NH_2$), diethylamine (($CH_3CH_2)_2NH$), butyl amine ($BuNH_2$).

At operation 118, the processing chamber is optionally purged after exposure to the reactant. Purging the processing chamber in operation 118 can be the same process or different process than the purge in operation 114. Purging the processing chamber, portion of the processing chamber, area adjacent the substrate surface, etc., removes unreacted reactant, reaction products and by-products from the area adjacent the substrate surface.

At decision 120, the thickness of the deposited film, or number of cycles of molybdenum-precursor and reactant is considered. If the deposited film has reached a predetermined thickness or a predetermined number of process cycles have been performed, the method 100 moves to an optional post-processing operation 130. If the thickness of the deposited film or the number of process cycles has not reached the predetermined threshold, the method 100 returns to operation 110 to expose the substrate surface to the molybdenum precursor again in operation 112, and continuing.

The optional post-processing operation 130 can be, for example, a process to modify film properties (e.g., annealing) or a further film deposition process (e.g., additional ALD or CVD processes) to grow additional films. In some embodiments, the optional post-processing operation 130 can be a process that modifies a property of the deposited film. In some embodiments, the optional post-processing operation 130 comprises annealing the as-deposited film. In some embodiments, annealing is done at temperatures in the range of about 300° C., 400° C., 500° C., 600° C., 700° C., 800° C., 900° C. or 1000° C. The annealing environment of some embodiments comprises one or more of an inert gas (e.g., molecular nitrogen ($N_2$), argon (Ar)) or a reducing gas (e.g., molecular hydrogen ($H_2$) or ammonia ($NH_3$)) or an oxidant, such as, but not limited to, oxygen ($O_2$), ozone ($O_3$), or peroxides. Annealing can be performed for any suitable length of time. In some embodiments, the film is annealed for a predetermined time in the range of about 15 seconds to about 90 minutes, or in the range of about 1 minute to about 60 minutes. In some embodiments, annealing the as-deposited film increases the density, decreases the resistivity and/or increases the purity of the film. In one or more embodiments, annealing can also with performed with a gas under plasma. In one or more embodiments, the annealing temperature may be lower with plasma.

In one or more embodiments, the plasma comprises one or more of nitrogen ($N_2$), argon (Ar), helium (He), hydrogen ($H_2$), carbon monoxide (CO), carbon dioxide ($CO_2$) methane ($CH_4$), and ammonia ($NH_3$). In some embodiments, the plasma is a remote plasma. In other embodiments, the plasma is a direct plasma.

In one or more embodiments, the plasma may be generated remotely or within the processing chamber. In one or more embodiments, the plasma is an inductively coupled plasma (ICP) or a conductively coupled plasma (CCP). Any suitable power can be used depending on, for example, the reactants, or the other process conditions. In some embodiments, the plasma is generated with a plasma power in the range of about 10 W to about 3000 W. In some embodiments, the plasma is generated with a plasma power less than or equal to about 3000 W, less than or equal to about 2000 W, less than or equal to about 1000 W, less than or equal to about 500 W, or less than or equal to about 250 W.

The method 100 can be performed at any suitable temperature depending on, for example, the molybdenum precursor, reactant or thermal budget of the device. In one or more embodiments, the use of high temperature processing may be undesirable for temperature-sensitive substrates, such as logic devices. In some embodiments, exposure to the molybdenum precursor (operation 112) and the reactant (operation 116) occur at the same temperature. In some embodiments, the substrate is maintained at a temperature in a range of about 20° C. to about 400° C., or about 50° C. to about 650° C.

In some embodiments, exposure to the molybdenum precursor (operation 112) occurs at a different temperature than the exposure to the reactant (operation 116). In some embodiments, the substrate is maintained at a first temperature in a range of about 20° C. to about 400° C., or about 50° C. to about 650° C., for the exposure to the molybdenum precursor, and at a second temperature in the range of about 20° C. to about 400° C., or about 50° C. to about 650° C., for exposure the reactant.

In the embodiment illustrated in FIG. 1, at deposition operation 110 the substrate (or substrate surface) is exposed to the molybdenum precursor and the reactant sequentially. In another, un-illustrated, embodiment, the substrate (or substrate surface) is exposed to the molybdenum precursor and the reactant simultaneously in a CVD reaction. In a CVD reaction, the substrate (or substrate surface) can be exposed to a gaseous mixture of the molybdenum precursor and reactant to deposit a molybdenum-containing film having a predetermined thickness. In the CVD reaction, the molybdenum-containing film can be deposited in one exposure to the mixed reactive gas, or can be multiple exposures to the mixed reactive gas with purges between.

In some embodiments, the molybdenum-containing film formed comprises elemental molybdenum. Stated differently, in some embodiments, the molybdenum-containing film comprises a metal film comprising molybdenum. In some embodiments, the metal film consists essentially of molybdenum. As used in this manner, the term "consists essentially of molybdenum" means that the molybdenum-containing film is greater than or equal to about 80%, 85%, 90%, 95%, 98%, 99% or 99.5% molybdenum, on an atomic basis. Measurements of the composition of the molybdenum-containing film refer to the bulk portion of the film, excluding interface regions where diffusion of elements from adjacent films may occur.

In other embodiments, the molybdenum-containing film comprises molybdenum oxide ($MoO_x$) with an oxygen content of greater than or equal to about 5%, 7.5%, 10%, 12.5 or 15%, on an atomic basis. In some embodiments, the molybdenum-containing film comprises an oxygen content in the range of about 2% to about 30%, or in the range of about 3% to about 25%, or in the range of about 4% to about 20%, on an atomic basis.

In other embodiments, the molybdenum-containing film comprises molybdenum carbide ($MoC_x$) with a carbon content of greater than or equal to about 5%, 7.5%, 10%, 12.5 or 15%, on an atomic basis. In some embodiments, the molybdenum-containing film comprises a carbon content in the range of about 2% to about 30%, or in the range of about 3% to about 25%, or in the range of about 4% to about 20%, on an atomic basis.

The deposition operation 110 can be repeated to form one or more of a molybdenum oxide film, a molybdenum carbide film, a molybdenum silicide film, and a molybdenum nitride film, having a predetermined thickness. In some embodiments, the deposition operation 110 is repeated to provide one or more of a molybdenum oxide film, a molybdenum carbide film, a molybdenum silicide film, and a molybdenum nitride film having a thickness in the range of about 0.3 nm to about 100 nm, or in the range of about 30 Å to about 3000 Å.

One or more embodiments of the disclosure are directed to methods of depositing molybdenum-containing films in high aspect ratio features. A high aspect ratio feature is a trench, via or pillar having a height:width ratio greater than or equal to about 10, 20, or 50, or more. In some embodiments, the molybdenum-containing film is deposited conformally on the high aspect ratio feature. As used in this manner, a conformal film has a thickness near the top of the feature that is in the range of about 80-120% of the thickness at the bottom of the feature.

Some embodiments of the disclosure are directed to methods for bottom-up gapfill of a feature. A bottom-up gapfill process fills the feature from the bottom versus a conformal process which fills the feature from the bottom and sides. In some embodiments, the feature has a first material at the bottom (e.g., a nitride) and a second material (e.g., an oxide) at the sidewalls. The molybdenum-containing film deposits selectively on the first material relative to the second material so that the molybdenum film fills the feature in a bottom-up manner.

According to one or more embodiments, the substrate is subjected to processing prior to and/or after forming the layer. This processing can be performed in the same chamber or in one or more separate processing chambers. In some embodiments, the substrate is moved from the first chamber to a separate, second chamber for further processing. The substrate can be moved directly from the first chamber to the separate processing chamber, or it can be moved from the first chamber to one or more transfer chambers, and then moved to the separate processing chamber. Accordingly, the processing apparatus may comprise multiple chambers in communication with a transfer station. An apparatus of this sort may be referred to as a "cluster tool" or "clustered system," and the like.

Generally, a cluster tool is a modular system comprising multiple chambers which perform various functions including substrate center-finding and orientation, degassing, annealing, deposition and/or etching. According to one or more embodiments, a cluster tool includes at least a first chamber and a central transfer chamber. The central transfer chamber may house a robot that can shuttle substrates between and among processing chambers and load lock chambers. The transfer chamber is typically maintained at a vacuum condition and provides an intermediate stage for shuttling substrates from one chamber to another and/or to a load lock chamber positioned at a front end of the cluster tool. Two well-known cluster tools which may be adapted for the present disclosure are the Centura® and the Endura®, both available from Applied Materials, Inc., of Santa Clara, Calif. However, the exact arrangement and combination of chambers may be altered for purposes of performing specific steps of a process as described herein. Other processing chambers which may be used include, but are not limited to, cyclical layer deposition (CLD), atomic layer deposition (ALD), chemical vapor deposition (CVD), physical vapor deposition (PVD), etch, pre-clean, chemical clean, thermal treatment such as RTP, plasma nitridation, degas, orientation, hydroxylation and other substrate processes. By carrying out processes in a chamber on a cluster tool, surface contamination of the substrate with atmospheric impurities can be avoided without oxidation prior to depositing a subsequent film.

According to one or more embodiments, the substrate is continuously under vacuum or "load lock" conditions, and is not exposed to ambient air when being moved from one chamber to the next. The transfer chambers are thus under vacuum and are "pumped down" under vacuum pressure. Inert gases may be present in the processing chambers or the transfer chambers. In some embodiments, an inert gas is used as a purge gas to remove some or all of the reactants (e.g., reactant). According to one or more embodiments, a purge gas is injected at the exit of the deposition chamber to prevent reactants (e.g., reactant) from moving from the deposition chamber to the transfer chamber and/or additional processing chamber. Thus, the flow of inert gas forms a curtain at the exit of the chamber.

The substrate can be processed in single substrate deposition chambers, where a single substrate is loaded, processed and unloaded before another substrate is processed. The substrate can also be processed in a continuous manner, similar to a conveyer system, in which multiple substrate are individually loaded into a first part of the chamber, move through the chamber and are unloaded from a second part of the chamber. The shape of the chamber and associated conveyer system can form a straight path or curved path. Additionally, the processing chamber may be a carousel in which multiple substrates are moved about a central axis and are exposed to deposition, etch, annealing, cleaning, etc. processes throughout the carousel path.

During processing, the substrate can be heated or cooled. Such heating or cooling can be accomplished by any suitable means including, but not limited to, changing the temperature of the substrate support and flowing heated or cooled gases to the substrate surface. In some embodiments, the substrate support includes a heater/cooler which can be controlled to change the substrate temperature conductively. In one or more embodiments, the gases (either reactive gases or inert gases) being employed are heated or cooled to locally change the substrate temperature. In some embodiments, a heater/cooler is positioned within the chamber adjacent the substrate surface to convectively change the substrate temperature.

The substrate can also be stationary or rotated during processing. A rotating substrate can be rotated (about the substrate axis) continuously or in discrete steps. For example, a substrate may be rotated throughout the entire process, or the substrate can be rotated by a small amount between exposures to different reactive or purge gases. Rotating the substrate during processing (either continuously or in steps) may help produce a more uniform deposition or etch by minimizing the effect of, for example, local variability in gas flow geometries.

The disclosure is now described with reference to the following examples. Before describing several exemplary embodiments of the disclosure, it is to be understood that the disclosure is not limited to the details of construction or process steps set forth in the following description. The disclosure is capable of other embodiments and of being practiced or being carried out in various ways.

EXAMPLES

Example 1: Preparation of tris[1,2-bis(dimethylphosphino)ethyl]molybdenum(0), [Mo{(Me$_2$PCH$_2$)$_2$}$_3$]

To a solution of bis(ethylbenzene)molybdenum(0) (200 mg, 0.64 mmol, 1 eq.) in toluene (10 mL) 1,2-bis(dimethylphosphino)ethane (292 mg, 1.95 mmol, 3 eq) was added. The resulting mixture was stirred at 100° C. for 96 h. The suspension was filtered, the residue washed with toluene (2×2 mL) and dried in vacuo to obtain the desired product as a pale white solid. Yield: 90% (319 mg).
$^1$H NMR (300 MHz, MeCN-d$_3$): δ 1.34 (s, 18H, P—CH$_3$), 1.20 (m, 12H, PCH$_2$CH$_2$P), 1.16 (s, 18H, P—CH$_3$). $^{31}$P NMR (161.9 MHz, MeCN-d$_3$): δ 39.5 (m).

Example 2: Preparation of bis(1,4,7-trimethyl-1,4,7-triazacyclononyl)molybdenum(0), [Mo({MeN(CH$_2$)$_2$}$_3$)$_2$]

To a suspension of sodium (94 mg, 4.10 mmol, 7 eq.) in tetrahydrofuran (10 mL) 1,4,7-trimethyl-1,4,7-triazacyclononane (200 mg, 1.76 mmol, 3 eq.) and [MoCl$_5$](160 mg, 0.59 mmol, 1 eq.) were added. The resulting mixture was stirred at ambient temperature for 48 h. The solid components were filtered off, the filtrate was evaporated to dryness and the residue was extracted with n-hexane (3×3 mL). The solvent was removed in vacuo and the desired product was obtained as a brown oil. Yield: 70% (180.0 mg).

$^1$H NMR (300 MHz, C$_6$D$_6$): δ 3.31 (s, 24H, NCH$_2$CH$_2$N), 1.69 ppm (s, 18H, N—CH$_3$). $^{13}$C{$^1$H} NMR (75.5 MHz, C$_6$D$_6$): δ 70.4 (NCH$_2$CH$_2$N), 26.8 ppm (N—CH$_3$).

Example 3: Preparation of tris(2,2'-bipyridil)molybdenum(0), [Mo{(NC$_5$H$_4$)$_2$}$_3$]

To a suspension of potassium (188 mg, 4.81 mmol, 6 eq.) in tetrahydrofuran (10 mL) bipyridine (376 mg, 2.41 mmol, 3 eq) and [Mo(THF)$_2$Cl$_4$] (300 mg, 0.80 mmol, 1 eq.) were added. The resulting mixture was stirred at ambient temperature for 48 h. The solid components were filtered off, the filtrate was evaporated to dryness and the residue was extracted with acetonitrile (3×3 mL). The resulting dark purple solution was stored at −28° C. for 24 h to obtain the desired product as dark purple crystals. Yield: 63% (285 mg).

$^1$H NMR (300 MHz, MeCN-d$_3$): δ 8.69 (d, $^3J_{HH}$=4.5 Hz, 3H, bipy), 8.44 (d, $^3J_{HH}$=7.7 Hz, 3H, bipy), 7.90 (t, $^3J_{HH}$=7.7 Hz, 3H, bipy), 7.39 ppm (t, $^3J_{HH}$=4.5 Hz, 3H, bipy).

Figure 3:
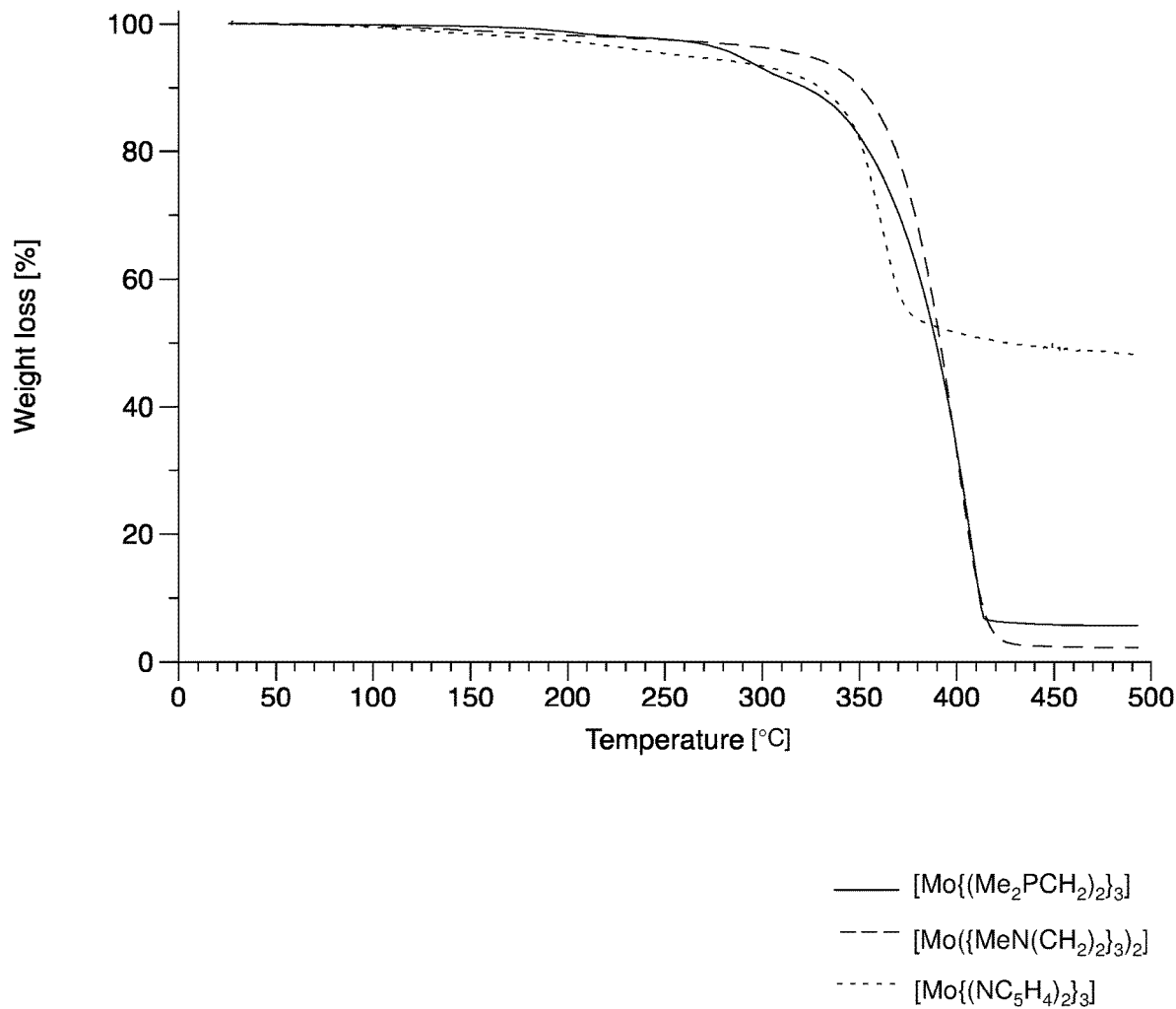
FIG. 3 illustrates thermogravimetric analysis data for the compounds of Examples 1-3.

FIG. 3 illustrates thermogravimetric analysis data for the compounds of Examples 1-3.

Example 4: Atomic Layer Deposition of Molybdenum Containing Films

General procedure: A silicon substrate is placed in a processing chamber. A molybdenum precursor is flowed into the processing chamber in an atmosphere of nitrogen (N$_2$) gas over the silicon substrate leaving a molybdenum-precursor terminated surface. Unreacted precursor and byproducts are then purged out of the chamber. Next, a co-reactant is then introduced into the chamber that reacts with the surface-bound molybdenum species. Again, excess coreactant and byproducts are removed from the chamber. The resultant material on the substrate is a molybdenum-containing film.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" may encompass both an orientation of above and below. The device may be otherwise oriented (rotated 90 degrees or at other orientations) and the spatially relative descriptors used herein interpreted accordingly.

The use of the terms "a" and "an" and "the" and similar referents in the context of describing the materials and methods discussed herein (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the materials and methods and does not pose a limitation on the scope unless otherwise claimed. No language in the specification should be construed as indicating any non-claimed element as essential to the practice of the disclosed materials and methods.

Reference throughout this specification to "one embodiment," "certain embodiments," "one or more embodiments" or "an embodiment" means that a particular feature, structure, material, or characteristic described in connection with the embodiment is included in at least one embodiment of the disclosure. Thus, the appearances of the phrases such as "in one or more embodiments," "in certain embodiments," "in one embodiment" or "in an embodiment" in various places throughout this specification are not necessarily referring to the same embodiment of the disclosure. In one or more embodiments, the particular features, structures, materials, or characteristics are combined in any suitable manner.

Although the disclosure herein has been described with reference to particular embodiments, it is to be understood that these embodiments are merely illustrative of the principles and applications of the present disclosure. It will be apparent to those skilled in the art that various modifications and variations can be made to the method and apparatus of the present disclosure without departing from the spirit and scope of the disclosure. Thus, it is intended that the present disclosure include modifications and variations that are within the scope of the appended claims and their equivalents.

What is claimed is:

1. A metal coordination complex consisting of a molybdenum(0) precursor having a general formula of Mo(L)$_z$, wherein z is 2, and L is selected from the group consisting of

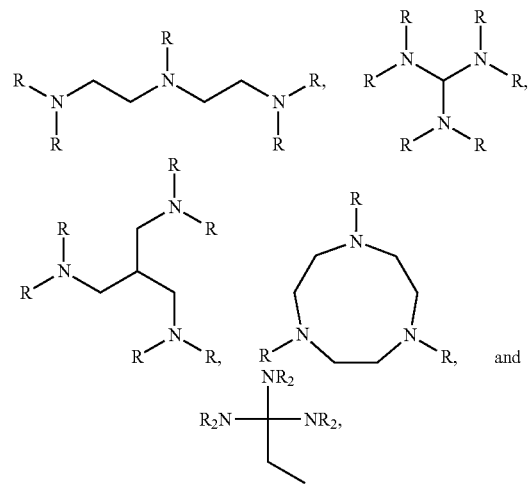

and wherein each R may be independently selected from Me-, Et-, iPr-, and tBu-.

* * * * *

UNITED STATES PATENT AND TRADEMARK OFFICE
CERTIFICATE OF CORRECTION

| | |
|---|---|
| PATENT NO. | : 12,060,370 B2 |
| APPLICATION NO. | : 17/146878 |
| DATED | : August 13, 2024 |
| INVENTOR(S) | : Andrea Leoncini et al. |

It is certified that error appears in the above-identified patent and that said Letters Patent is hereby corrected as shown below:

On the Title Page

Item (56) Column 2, Line 33, replace "16" after "addition of dehydration to (" and before "-" with "η6".

Signed and Sealed this
Fifteenth Day of October, 2024

Katherine Kelly Vidal
*Director of the United States Patent and Trademark Office*